United States Patent
Lee et al.

(10) Patent No.: US 10,244,969 B2
(45) Date of Patent: Apr. 2, 2019

(54) METHOD AND DEVICE FOR FINGERPRINT AUTHENTICATION

(71) Applicant: SUPREMA INC., Gyeonggi-do (KR)

(72) Inventors: Kideok Lee, Gyeonggi-do (KR); Hochul Shin, Gyeonggi-do (KR); Hyeonchang Lee, Gyeonggi-do (KR); Jong Man Lee, Gyeonggi-do (KR); Bong Seop Song, Gyeonggi-do (KR); Jae Won Lee, Gyeonggi-do (KR)

(73) Assignee: SUPREMA INC., Seongnam-si (KR)

( * ) Notice: Subject to any disclaimer, the term of this patent is extended or adjusted under 35 U.S.C. 154(b) by 99 days.

(21) Appl. No.: 15/633,117

(22) Filed: Jun. 26, 2017

(65) Prior Publication Data
US 2018/0008171 A1 Jan. 11, 2018

(30) Foreign Application Priority Data
Jul. 5, 2016 (KR) .................. 10-2016-0084953

(51) Int. Cl.
| | | |
|---|---|---|
| *G06K 9/00* | (2006.01) | |
| *A61B 5/1172* | (2016.01) | |
| *G07C 9/00* | (2006.01) | |
| *A61B 5/00* | (2006.01) | |

(52) U.S. Cl.
CPC .......... *A61B 5/1172* (2013.01); *A61B 5/6826* (2013.01); *A61B 5/6898* (2013.01); *A61B 5/7221* (2013.01); *G06K 9/0012* (2013.01); *G06K 9/00013* (2013.01); *G06K 9/00087* (2013.01); *G07C 9/00563* (2013.01); *A61B 2503/12* (2013.01)

(58) Field of Classification Search
None
See application file for complete search history.

(56) References Cited

U.S. PATENT DOCUMENTS

| 2004/0052405 | A1* | 3/2004 | Walfridsson | G06K 9/00087 382/115 |
|---|---|---|---|---|
| 2004/0228508 | A1* | 11/2004 | Shigeta | G06K 9/00026 382/124 |
| 2005/0152584 | A1* | 7/2005 | Svedin | G06F 21/32 382/124 |

(Continued)

FOREIGN PATENT DOCUMENTS

| KR | 10-2007-0019363 | 2/2007 |
|---|---|---|
| KR | 10-2016-0018318 | 5/2016 |

*Primary Examiner* — Hadi Akhavannik
(74) *Attorney, Agent, or Firm* — Brinks Gilson & Lione (57) ABSTRACT

A fingerprint authentication method includes a first step of acquiring partial fingerprint measurement data for a part of a fingerprint, and a second step of calculating a matching rate by comparing the partial fingerprint measurement data with reference comparison data selected among a plurality of partial fingerprint registration data, each partial fingerprint registration data corresponding to a part of a fingerprint. The method further includes a third step of determining whether the matching rate is equal to or greater than an authentication threshold and a fourth step of determining, based on a result in the third step, a success of the authentication, or repeating the second and third steps by selecting new reference comparison data based on whether or not the matching rate is equal to or greater than a preset threshold smaller than the authentication threshold.

16 Claims, 3 Drawing Sheets

(56) References Cited

U.S. PATENT DOCUMENTS

| | | | |
|---|---|---|---|
| 2007/0253608 A1* | 11/2007 | Tulyakov | G06K 9/00073 |
| | | | 382/125 |
| 2007/0292008 A1* | 12/2007 | Yumoto | G06K 9/00087 |
| | | | 382/124 |
| 2016/0203354 A1* | 7/2016 | Choi | G06K 9/00026 |
| | | | 382/124 |
| 2016/0314337 A1* | 10/2016 | Suh | G06K 9/00013 |
| 2017/0344802 A1* | 11/2017 | Zhang | G06F 21/32 |
| 2017/0372051 A1* | 12/2017 | Lee | G06F 21/32 |

* cited by examiner

METHOD AND DEVICE FOR FINGERPRINT AUTHENTICATION

CROSS-REFERENCE TO RELATED APPLICATIONS

This application is based on and claims priority from Korean Patent Application No. 10-2016-0084953, filed on Jul. 5, 2016, the disclosure of which is incorporated herein in its entirety by reference.

TECHNICAL FIELD

The present disclosure relates to a fingerprint authentication method and a fingerprint authentication device, and more particularly, to a fingerprint authentication method and a fingerprint authentication device for processing a fingerprint authentication by using partial fingerprint measurement data corresponding to a part of an entire fingerprint.

BACKGROUND

As is well known in the art, biometric features currently used for authentication purposes in a biometric authentication system include fingerprints, facial patterns, voice patterns, hand measurements, eye retinas and irises, vein patterns and the like, and researches and studies on each of these features have been actively conducted.

In recent years, biometric authentication has been adopted for portable electronic devices such as smartphones and the like, and fingerprint authentication has been widely adopted among various types of biometric authentication for such portable electronic devices. The fingerprint authentication has advantages of high security level and usability compared to other biometric authentication techniques.

However, a fingerprint sensor installed in the portable electronic device such as smartphones is very small in size due to cost savings and space limitations, and therefore, only a very small portion of a fingerprint may be inputted at a time.

As the fingerprint sensor becomes smaller, the size of the fingerprint images captured for authentication purpose and registration purpose also becomes smaller, so that the amount of fingerprint information is also reduced. Further, a portion of the fingerprint inputted when registering in advance the fingerprint data for authentication procedure and a portion of the fingerprint inputted when the authentication is requested may be completely different from each other. Thus, it may often occur in practice that a fingerprint overlap area does not exist.

Particularly, the use of such a small-size fingerprint sensor may lead to an undesirably high false rejection rate (FRR). In order to prevent the increase of the false rejection rate in measuring and sensing such a small-size fingerprint at the time of authentication, a plurality of fingerprint data for different parts of an entire fingerprint are registered and stored in multiple times when registering in advance the fingerprint data to be used in the authentication procedure.

When a large number of fingerprint data are registered in advance and used for the authentication procedure, authentication performance may be improved. However, this may also increase an authentication processing time, which is problematic. Although improving a performance of a central processing unit (CPU) such as an application processor (AP) of the smartphone may reduce the increase of the authentication processing time, this leads to an increase of a manufacturing cost.

Reference Document: Korean Patent No. 0846403

In view of the above, the present disclosure provides a method and a device for fingerprint authentication, which are capable of rapidly and quickly selecting appropriate and optimal reference comparison data among a plurality of partial fingerprint registration data registered in advance when an authentication is performed on partial fingerprint measurement data measured for a part of the entire fingerprint area.

However, aspects of the present disclosure are not restricted to those set forth herein. The above and other aspects of the present disclosure will become more apparent to one of ordinary skill in the art to which the present disclosure pertains by referencing the detailed description of the present disclosure given below.

SUMMARY

In accordance with an aspect of the present disclosure, there is provided a fingerprint authentication method performed by a fingerprint authentication device, the fingerprint authentication method including: acquiring partial fingerprint measurement data measured for authentication, which corresponds to a part of a fingerprint; calculating a matching rate by comparing the partial fingerprint measurement data with reference comparison data selected among a plurality of partial fingerprint registration data stored in advance, each of the plurality of partial fingerprint registration data corresponding to a part of a fingerprint; first determining whether the matching rate is equal to or greater than a predetermined authentication threshold; and second determining, based on a result in the first determining, a success of the authentication to complete the authentication, or repeating the calculating and the first determining by selecting new reference comparison data among the partial fingerprint registration data that have not been selected as the reference comparison data based on whether or not the matching rate is equal to or greater than a preset threshold, which is smaller than the predetermined authentication threshold.

Further, the reference comparison data may be selected based on a sum or an average of matching rates which are calculated by matching each of the partial fingerprint registration data with all of the other partial fingerprint registration data or based on the number of matched data when matching each of the partial fingerprint registration data with all of the other partial fingerprint registration data.

Further, in the repeating, if the matching rate is equal to or greater than the preset threshold, one of the plurality of partial fingerprint registration data whose matching rate with the reference comparison data previously used is equal to or greater than a first threshold may be selected as the new reference comparison data, and if the matching rate is smaller than the preset threshold, one of the plurality of partial fingerprint registration data whose matching rate with the reference comparison data previously used is smaller than a second threshold may be selected as the new reference comparison data.

Further, the second threshold may be equal to or smaller than the first threshold.

Further, the matching rate may be calculated based on a similarity between the partial fingerprint measurement data and the reference comparison data or based on a matching area between the partial fingerprint measurement data and the reference comparison data.

Further, the fingerprint authentication method described above may further include: defining an entire fingerprint area that is formed by arranging all of the plurality of partial fingerprint registration data to overlap common regions therebetween; acquiring, if the matching rate is smaller than the predetermined authentication threshold, a comparison fingerprint area by arranging all of the partial fingerprint registration data that have been selected as the reference comparison data to overlap common regions therebetween; and determining and outputting a failure of the authentication when a ratio of the comparison fingerprint area to the entire fingerprint area is equal to or greater than a predetermined value.

Further, one of the plurality of partial fingerprint registration data may be selected as the reference comparison data depending on a distance from a center of the entire fingerprint area.

In accordance with another aspect of the present disclosure, there is provided a computer program stored on a non-transitory computer-readable storage medium which, when executed by a processor, performs the fingerprint authentication method described above.

In accordance with still another aspect of the present disclosure, there is provided a non-transitory computer-readable storage medium storing instructions which, when executed by a processor, perform the fingerprint authentication method described above.

In accordance with still another aspect of the present disclosure, there is provided a data storage unit configured to store a plurality of partial fingerprint registration data, each of which corresponds to a part of a fingerprint; a data input unit configured to receive partial fingerprint measurement data for an authentication, which corresponds to a part of a fingerprint; a control unit configured to perform the authentication by comparing the plurality of partial fingerprint registration data and the partial fingerprint measurement data; and an output unit configured to output a result of the authentication under a control of the control unit. The control unit performs steps of: calculating a matching rate by comparing the partial fingerprint measurement data with reference comparison data selected among the plurality of partial fingerprint registration data; first determining whether the matching rate is equal to or greater than a predetermined authentication threshold; and second determining, based on a result in the step of first determining, a success of the authentication to complete the authentication, or repeating the calculating step and the first determining step by selecting new reference comparison data among the partial fingerprint registration data that have not been selected as the reference comparison data based on whether or not the matching rate is equal to or greater than a preset threshold, which is smaller than the predetermined authentication threshold.

Further, the control unit may be configured to select the reference comparison data based on a sum or an average of matching rates which are calculated by matching each of the partial fingerprint registration data with all of the other partial fingerprint registration data or based on the number of matched data when matching each of the partial fingerprint registration data with all of the other partial fingerprint registration data.

Further, in the repeating step, if the matching rate is equal to or greater than the preset threshold, one of the plurality of partial fingerprint registration data whose matching rate with the reference comparison data previously used is equal to or greater than a first threshold may be selected as the new reference comparison data, and if the matching rate is smaller than the preset threshold, one of the plurality of partial fingerprint registration data whose matching rate with the reference comparison data previously used is smaller than a second threshold may be selected as the new reference comparison data.

Further, the second threshold may be equal to or smaller than the first threshold.

Further, the matching rate may be calculated based on a similarity between the partial fingerprint measurement data and the reference comparison data or based on a matching area between the partial fingerprint measurement data and the reference comparison data.

Further, the control unit may further perform steps of: defining an entire fingerprint area that is formed by arranging all of the plurality of partial fingerprint registration data to overlap common regions therebetween; acquiring, if the matching rate is smaller than the predetermined authentication threshold, a comparison fingerprint area by arranging all of the partial fingerprint registration data that have been selected as the reference comparison data to overlap common regions therebetween; and determining and outputting a failure of the authentication a ratio of the comparison fingerprint area to the entire fingerprint area is equal to or greater than a predetermined value.

Further, one of plurality of the partial fingerprint registration data may be selected as the reference comparison data depending on a distance from a center of the entire fingerprint area.

In accordance with the embodiment, when the authentication is performed on partial fingerprint measurement data measured for a part of the entire fingerprint area, appropriate and optimal reference comparison data can be rapidly and quickly selected among the plurality of partial fingerprint registration data registered in advance.

Therefore, even though a large number of a plurality of partial fingerprint registration data are registered and stored for authentication, a processing time until the authentication is permitted is reduced while an authentication performance is not degraded.

BRIEF DESCRIPTION OF THE DRAWINGS

The objects and features of the present disclosure will become apparent from the following description of embodiments, given in conjunction with the accompanying drawings, in which.

DETAILED DESCRIPTION

Advantages and features of the present disclosure, and a method for achieving them will be apparent with reference to the embodiments described herein below in detail together with accompanying drawings. However, it should be noted that the present disclosure is not limited to the embodiments disclosed herein below, but may be implemented in various forms. It should be noted that the embodiments are provided to make the description of the present disclosure complete, and assist those skilled in the art of the present disclosure to understand the scope of present disclosure, defined just by the scope of the claims.

In the following description, well-known functions and/or constitutions will not be described in detail if they would unnecessarily obscure the features of the present disclosure in unnecessary detail. Further, the terms to be described below are defined in consideration of their functions in the embodiments of the present disclosure and may vary depending on the intention of a user or an operator and the practice. Accordingly, the definition may be made on the basis of the content throughout the specification.

Figure 1:
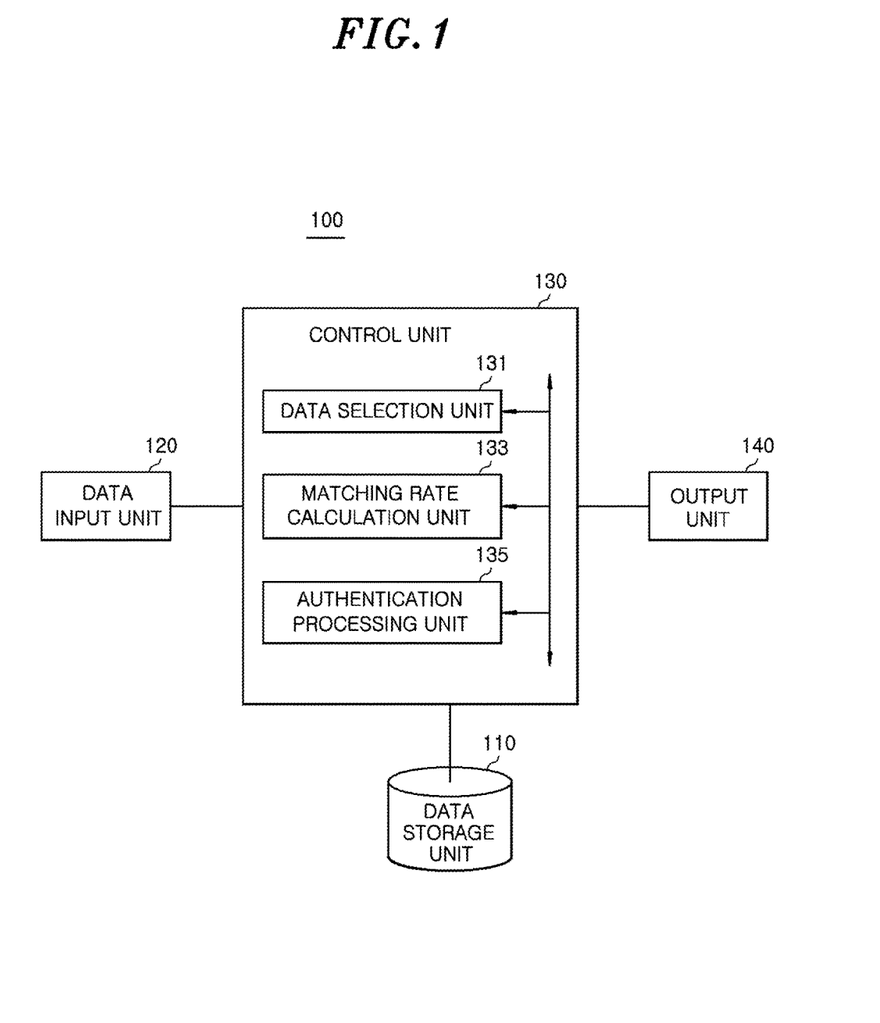
FIG. 1 is a block diagram of a fingerprint authentication device capable of performing a fingerprint authentication method in accordance with an embodiment of the present disclosure.

FIG. 1 is a block diagram of a fingerprint authentication device capable of performing a fingerprint authentication method in accordance with an embodiment of the present disclosure.

A fingerprint authentication device 100 includes a data storage unit 110, a data input unit 120, a control unit 130, and an output unit 140. The control unit 130 includes a data selection unit 131, a matching rate calculation unit 133, and an authentication processing unit 135.

In the data storage unit 110, a plurality of partial fingerprint registration data for different portions of a fingerprint are registered and stored in advance. Here, each partial fingerprint registration data corresponds to a part of a single fingerprint. Further, in the data storage unit 110, information on relationships between the plurality of partial fingerprint registration data may also be stored. Each partial fingerprint registration data may be stored after being converted into a template form through feature extraction and encryption. Further, the information on relationships between the plurality of partial fingerprint registration data may include identification information on a template having a common region with another template, information on an intersection of common regions, information on a plane angle of a template in a fingerprint image, and the like. The data storage unit 110 may be implemented as a memory device such as an electrically erasable programmable read-only memory (EEPROM).

The data input unit 120 is configured to obtain a partial fingerprint measurement data by measuring a part of the fingerprint and transmit the obtained partial fingerprint measurement data to the control unit 130. Here, the partial fingerprint measurement data corresponds to a part of a single fingerprint. This data input unit 120 may be a fingerprint scanning device for capturing a fingerprint image. Alternatively, the data input unit 120 may be a communication interface for receiving fingerprint image data from a separately-installed fingerprint sensor.

The control unit 130 is configured to perform a fingerprint authentication by comparing the plurality of partial fingerprint registration data stored in the data storage unit 110 and the partial fingerprint measurement data inputted through the data input unit 120. Here, the fingerprint image obtained from the data input unit 120 may be fingerprint data, having a size of 10 mm×10 mm or less, corresponding to a part of the fingerprint. The control unit 130 may be implemented as a processor such as a central processing unit (CPU).

The data selection unit 131 is configured to select one of the plurality of partial fingerprint registration data as reference comparison data to be used in authentication for a currently inputted partial fingerprint measurement data. Specifically, the data selection unit 131 selects the reference comparison data in such a manner that a sum or an average of matching rates or the number of matched data is calculated by matching each partial fingerprint registration data with all of the other partial fingerprint registration data and, based thereon, one of the plurality of partial fingerprint registration data is selected as the reference comparison data. Here, the initial reference comparison data may be determined before the partial fingerprint measurement data is inputted through the data input unit 120 since it is determined on the basis of the information on relationships between the plurality of partial fingerprint registration data registered in the data storage unit 110. For example, partial fingerprint registration data (e.g., a template at a center region shown in FIG. 3), which has the largest number of common regions with other partial fingerprint registration data (other templates), is determined as the initial reference comparison data before the partial fingerprint measurement data is inputted.

The matching rate calculation unit 133 is configured to calculate matching rates by matching each partial fingerprint registration data with all of the other partial fingerprint registration data and calculate a sum and an average of the calculated matching rates. In addition, the number of matched data is calculated. The calculated results from the matching rate calculation unit 133 may be provided to the data selection unit 131 so that the data selection unit 131 selects the reference comparison data based thereon. The matching rate calculation unit 133 is further configured to calculate a matching rate between the partial fingerprint measurement data and the selected reference comparison data on the basis of the similarity or matching area therebetween.

The authentication processing unit 135 is configured to compare the matching rate calculated by the matching rate calculation unit 133 with a predetermined authentication threshold to determine whether or not the authentication is successful. Specifically, the authentication processing unit 135 determines whether the matching rate calculated by the matching rate calculation unit 133 is equal to or greater than the predetermined authentication threshold. When it is determined that the matching rate is equal to or greater than the predetermined authentication threshold, the authentication processing unit 135 determines the success of the authentication to complete the authentication. When it is determined that the matching rate is smaller than the predetermined authentication threshold, new reference comparison data is selected, among the partial fingerprint data that have not been selected, based on whether or not the matching rate is equal to or greater than a preset threshold to be described later, which is smaller than the authentication threshold, and the calculation of the matching rate and the subsequent processes are executed again.

Further, when it is determined that the matching rate is smaller than the predetermined authentication threshold, the authentication processing unit 135 may immediately determine the failure of the authentication before using the preset threshold if an additional condition as described below is satisfied.

Specifically, the authentication processing unit 135 defines an entire fingerprint area that is formed by arranging all of the plurality of partial fingerprint registration data registered and stored in advance in the data storage unit 110 such that the common regions thereof are overlapped with one another. Then, the authentication processing unit 135 acquires a comparison fingerprint area that is formed by arranging all of the partial fingerprint registration data that have been selected as the reference comparison data such that common regions thereof are overlapped with one another. The failure of the authentication is determined and outputted if a ratio of the comparison fingerprint area to the entire fingerprint area is equal to or greater than a predetermined value. On the other hand, if the authentication processing unit 135 determines that the ratio of the comparison fingerprint area to the entire fingerprint area is smaller than the predetermined value, the data selecting unit 131 selects new reference comparison data to be used for the fingerprint authentication among the remaining partial fingerprint registration data which have not been selected as the reference comparison data until then.

When selecting the new reference comparison data, the data selection unit 131 may determine whether the matching rate calculated by the matching rate calculation unit 133 is equal to or greater than the preset threshold. If it is determined that the matching rate calculated by the matching rate calculation unit 133 is equal to or greater than the preset threshold, the data selecting unit 131 selects as the new reference comparison data one of the remaining partial fingerprint registration data whose matching rate with the previous reference comparison data (e.g., the initial reference comparison data) is equal to or greater than a first threshold. On the other hand, if it is determined that the matching rate calculated by the matching rate calculation unit 133 is smaller than the preset threshold, the data selecting unit 131 selects as the new reference comparison data one of the remaining partial fingerprint registration data whose matching rate with the previous reference comparison data is smaller than a second threshold. Here, the second threshold may be equal to or smaller than the first threshold.

When the matching rate is equal to or greater than the predetermined authentication threshold, the authentication processing unit 135 determines that the fingerprint authentication has succeeded and the output unit 140 outputs the success of the authentication. When the matching rate is smaller than the predetermined authentication threshold while the ratio of the comparison fingerprint area to the entire fingerprint area is equal to or greater than the predetermined value, the authentication processing unit 135 determines that the fingerprint authentication has failed and the output unit 140 outputs the failure of the authentication.

Here, when the reference comparison data is initially selected, the matching rate calculation unit 133 calculates matching rates by matching each partial fingerprint registration data with all of the other partial fingerprint registration data on the basis of the information on relationships between the plurality of partial fingerprint registration data registered in the data storage unit 110. Then, the data selection unit 131 selects the initial reference comparison data among the plurality of partial fingerprint registration data registered in advance based on the sum or the average of the calculated matching rates or the number of matched data.

The output unit 140, when the control unit 130 determines the success or the failure of the fingerprint authentication for the inputted partial fingerprint measurement data, outputs the determination result on a screen or through a voice. For example, the output unit 140 may be implemented as a display device or a speaker.

Figure 2:
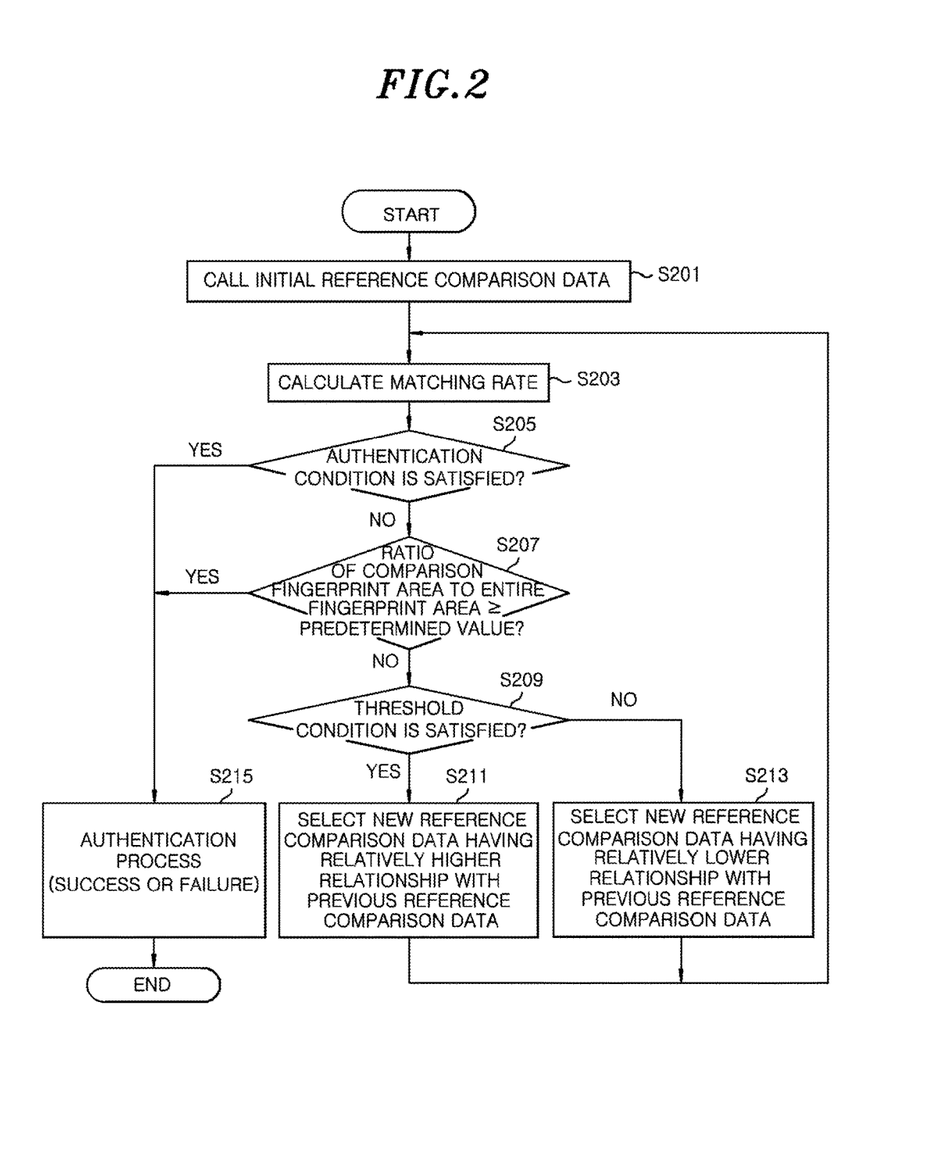
FIG. 2 is a flowchart for explaining the fingerprint authentication method in accordance with the embodiment of the present disclosure.
Figure 3:
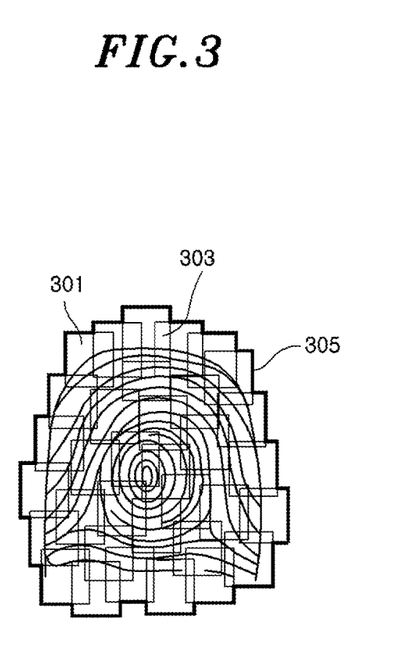
FIG. 3 shows an example in which a plurality of partial fingerprint registration data are arranged for defining an entire fingerprint area in accordance with the embodiment of the present disclosure.

FIG. 2 is a flowchart for explaining a fingerprint authentication method in accordance with an embodiment of the present disclosure. FIG. 3 shows an example in which a plurality of partial fingerprint registration data are arranged for defining an entire fingerprint area in accordance with an embodiment of the present disclosure. Hereinafter, the fingerprint authentication method in accordance with the embodiment of the present disclosure will be described with reference to FIGS. 1 to 3.

First, a plurality of partial fingerprint registration data for different portions of a fingerprint to be authenticated are registered and stored in advance in the data storage unit 110 together with information on relationships between the plurality of partial fingerprint registration data. Here, each partial fingerprint registration data may be stored in the data storage unit 110 after being converted into a template form through feature extraction and encryption. Further, the information on relationships between the plurality of partial fingerprint registration data stored in the data storage unit 110 may include identification information on a template having a common region with another template, information on an intersection of common regions, information on a plane angle of a template in a fingerprint image, and the like.

Partial fingerprint measurement data measured for authentication is obtained by the data input unit 120 in a state where the plurality of partial fingerprint registration data to be used for fingerprint authentication are registered in advance.

When the authentication for the partial fingerprint measurement data is requested, the data selection unit 131 of the control unit 130 selects one of the plurality of partial fingerprint registration data as the initial reference comparison data to be used for the fingerprint authentication. To this end, the matching rate calculation unit 133 of the control unit 130 calculates matching rates by matching each partial fingerprint registration data with all of the other partial fingerprint registration data on the basis of the information on relationships between the plurality of partial fingerprint registration data, and provides the calculated matching rates to the data selection unit 131. For example, the matching rate calculation unit 133 compares a plurality of partial fingerprint registration data (templates) with each other in a one-to-many relationship manner to calculate, e.g., similarities therebetween, the matching area therebetween, or a ratio of the matching area therebetween to the entire area of partial fingerprint registration data. Then, the calculated results may be provided as the matching rates to the data selection unit 131 from the matching rate calculation unit 133. Further, the matching rate calculation unit 133 may provide the data selection unit 131 with a sum or an average of the matching rates calculated for each partial fingerprint registration data with respect to all of the other partial fingerprint registration data. In addition, the matching rate calculation unit 133 may provide the data selection unit 131 with information on the number of matched data, which indicates how many partial fingerprint registration data are matched with each partial fingerprint registration data.

Thereafter, the data selection unit 131 selects, as the initial reference comparison data to be used for the fingerprint authentication, one of the plurality of partial fingerprint registration data having the highest matching rate with the other fingerprint partial registration data (step S201). At this time, the initial reference comparison data may be selected based on the sum or the average of the matching rates, or the number of matched data. However, since the initial reference comparison data is determined on the basis of the information on relationships between the plurality of partial fingerprint registration data, it may be determined before the partial fingerprint measurement data is inputted.

Next, the matching rate calculation unit 133 calls the selected reference comparison data, e.g., the initial reference comparison data, to calculate a matching rate by comparing the partial fingerprint measurement data acquired through the data input unit 120 with the selected reference comparison data. Here, the matching rate calculation unit 133 may obtain the matching rate by calculating a similarity between the partial fingerprint measurement data and the selected reference comparison data, the matching area between the partial fingerprint measurement data and the selected reference comparison data, or a ratio of the matching area therebetween to the entire area of the partial fingerprint measurement data (steps S201 and S203).

Then, the authentication processing unit 135 of the control unit 130 determines whether the matching rate calculated by the matching rate calculation unit 133 in step S203 satisfies a predetermined authentication condition to determine a success of the authentication (step S205). For example, if the matching rate is greater than an authentication threshold, it is determined that the matching rate satisfies the predetermined authentication condition ('YES' in step S205). When the matching rate satisfies the predetermined authentication condition, the authentication processing unit 135 determines that the authentication for the partial fingerprint measurement data inputted through the data input unit 120 has succeeded, and the output unit 140 outputs the success of the authentication (step S215).

If the authentication processing unit 135 determines that the matching rate fails to satisfy the predetermined authentication condition ('NO' in step S205), the data selection unit 131 determines whether a ratio of a comparison fingerprint area to an entire fingerprint area is equal to or greater than a predetermined value (step S207).

Here, as shown in FIG. 3, the entire fingerprint area is an area surrounded by an outline 305 when all of the plurality of partial fingerprint registration data 301 registered and stored in advance in the data storage unit 110 are arranged so as to overlap common regions 303 therebetween.

Specifically, the authentication processing unit 135 defines the entire fingerprint area that is formed by arranging all of the plurality of partial fingerprint registration data registered and stored in advance in the data storage unit 110 such that the common regions thereof are overlapped with one another. Then, the authentication processing unit 135 acquires the comparison fingerprint area by arranging all of the partial fingerprint registration data that have been selected as the reference comparison data such that common regions thereof are overlapped with one another. Thereafter, the entire fingerprint area is compared with the comparison fingerprint area to determine whether the ratio of the comparison fingerprint area to the entire fingerprint area is equal to or greater than the predetermined value.

Here, if it is determined in step S207 that the ratio of the comparison fingerprint area to the entire fingerprint area is equal to or greater than the predetermined value ('YES' in step S207), the authentication processing unit 135 determines that the authentication for the partial fingerprint measurement data inputted through the data input unit 120 has failed, and the output unit 140 outputs the failure of the authentication (step S215).

However, if it is determined in step S207 that the ratio of the comparison fingerprint area to the entire fingerprint area is smaller than the predetermined value, the data selection unit 131 selects new reference comparison data to be used for the fingerprint authentication among the plurality of partial fingerprint registration data registered in the data storage unit 110.

Here, when selecting the new reference comparison data, the data selection unit 131 determines whether the matching rate calculated in step S203 satisfies a predetermined threshold condition. Specifically, if the matching rate calculated in step S203 is greater than a preset threshold which is smaller than the authentication threshold, it is determined that the matching rate satisfies the predetermined threshold condition.

When the matching rate calculated in step S203 satisfies the predetermined threshold condition ('YES' in step S209), the data selection unit 131 selects, based on the information on relationships between the plurality of partial fingerprint registration data stored in the data storage unit 110, one of the plurality of partial fingerprint registration data having a relatively higher relationship with the previous reference comparison data as the new reference comparison data. For example, the data selection unit 131 calculates a similarity or a matching area between the previous reference comparison data used for comparison with the current partial fingerprint measurement data and each of the other partial fingerprint registration data that have not been selected as the reference comparison data. Then, one of the plurality of partial fingerprint registration data having the highest similarity or the largest matching area can be selected as the new reference comparison data (steps S209 and S211). Alternatively, in step S211, one of the partial fingerprint registration data whose matching rate with the previous reference comparison data is equal to or greater than a first threshold can be randomly selected as the new reference comparison data.

On the other hand, when the matching rate calculated in step S203 fails to satisfy the predetermined threshold condition ('NO' in step S209), the data selection unit 131 selects, based on the information on relationships between the plurality of partial fingerprint registration data stored in the data storage unit 110, one of the plurality of partial fingerprint registration data having a relatively lower relationship with the previous reference comparison data as the new reference comparison data. For example, the data selection unit 131 calculates a similarity or a matching area between the previous reference comparison data used for comparison with the current partial fingerprint measurement data and each of the other partial fingerprint registration data that have not been selected as the reference comparison data. Then, one of the plurality of partial fingerprint registration data having the lowest similarity or the smallest matching area can be selected as the new reference comparison data (steps S209 and S213). Alternatively, in step S213, one of the partial fingerprint registration data whose matching rate with the previous reference comparison data is smaller than a second threshold can be randomly selected as the new reference comparison data (step S213). Here, the second threshold may be equal to or smaller than the first threshold used in step S211.

Alternatively, when the data selection unit 131 selects new reference comparison data among the plurality of partial fingerprint registration data, the new reference comparison data may be determined depending on a distance from the center of the entire fingerprint area. For example, in step S211, one of the partial fingerprint registration data whose distance from the center of the entire fingerprint area is equal to or greater than a third threshold may be selected as the new reference comparison data. Further, in step S213, one of the partial fingerprint registration data whose distance from the center of the entire fingerprint area is less than a fourth threshold may be selected as the new reference comparison data. Here, the fourth threshold may be equal to or smaller than the third threshold used in step S211.

After the new reference comparison data is selected by the data selection unit 131, the matching rate calculation unit 133 calculates a new matching rate by comparing the partial fingerprint measurement data inputted through the data input unit 120 with the new reference comparison data selected in step S211 or step S213, and the processes from step S203 to step S215 are repeated under the control of the control unit 130.

As described above, in accordance with the embodiment of the present disclosure, when the authentication is performed on a partial fingerprint measurement data measured for a part of the entire fingerprint area, appropriate and optimal reference comparison data can be rapidly and quickly selected among the plurality of partial fingerprint registration data registered in advance.

Therefore, even though a plurality of partial fingerprint registration data are registered and stored for authentication, a processing time until the authentication is permitted is reduced while an authentication performance is not degraded.

The combinations of respective sequences of a flow diagram attached herein may be carried out by computer program instructions. Since the computer program instructions may be executed by processors of a general purpose computer, a special purpose computer, or other programmable data processing apparatus, the instructions, c executed by the processor of the computer or other programmable data processing apparatus, create means for performing functions described in the respective sequences of the sequence diagram. Since the computer program instructions, in order to implement functions in specific manner, may be stored in a memory useable or readable by the computer or the computer for other programmable data processing apparatus, the instruction stored in the memory useable or readable by a computer may produce manufacturing items including an instruction means for performing functions described in the respective sequences of the sequence diagram. Since the computer program instructions may be loaded in a computer or other programmable data processing apparatus, instructions, a series of sequences of which is executed in a computer or other programmable data processing apparatus to create processes executed by a computer to operate a computer or other programmable data processing apparatus, may provide operations for executing functions described in the respective sequences of the flow diagram.

Moreover, the respective sequences may indicate some of modules, segments, or codes including at least one executable instruction for executing a specific logical function(s). In some alternative embodiments, it is noted that the functions described in the sequences may run out of order. For example, two consecutive sequences may be substantially executed simultaneously or often in reverse order according to corresponding functions.

The above description just illustrates the technical idea of the present disclosure, and it will be understood by those skilled in the art to which this present disclosure belongs that various changes and modifications may be made without departing from the scope of the essential characteristics of the present disclosure. Therefore, the exemplary embodiments disclosed herein are not used to limit the technical idea of the present disclosure, but to explain the present disclosure, and the scope of the technical idea of the present disclosure is not limited by those embodiments. Therefore, the scope of protection of the present disclosure should be construed as defined in the following claims, and all technical ideas that fall within the technical idea of the present disclosure are intended to be embraced by the scope of the claims of the present disclosure.

What is claimed is:

1. A fingerprint authentication method performed by a fingerprint authentication device, the fingerprint authentication method comprising:
  acquiring partial fingerprint measurement data measured for authentication, which corresponds to a part of a fingerprint;
  calculating a matching rate by comparing the partial fingerprint measurement data with reference comparison data selected among a plurality of partial fingerprint registration data stored in advance, each of the plurality of partial fingerprint registration data corresponding to a part of a fingerprint;
  first determining whether the matching rate is equal to or greater than a predetermined authentication threshold; and
  second determining, based on a result in said first determining, a success of the authentication to complete the authentication, or repeating said calculating and said first determining by selecting new reference comparison data among the partial fingerprint registration data that have not been selected as the reference comparison data based on whether or not the matching rate is equal to or greater than a preset threshold, which is smaller than the predetermined authentication threshold.

2. The fingerprint authentication method of claim 1, wherein the reference comparison data is selected based on a sum or an average of matching rates which are calculated by matching each of the partial fingerprint registration data with all of the other partial fingerprint registration data or based on the number of matched data when matching each of the partial fingerprint registration data with all of the other partial fingerprint registration data.

3. The fingerprint authentication method of claim 1, wherein, in said repeating, if the matching rate is equal to or greater than the preset threshold, one of the plurality of partial fingerprint registration data whose matching rate with the reference comparison data previously used is equal to or greater than a first threshold is selected as the new reference comparison data, and
  if the matching rate is smaller than the preset threshold, one of the plurality of partial fingerprint registration data whose matching rate with the reference comparison data previously used is smaller than a second threshold is selected as the new reference comparison data.

4. The fingerprint authentication method of claim 1, wherein the second threshold is equal to or smaller than the first threshold.

5. The fingerprint authentication method of claim 1, wherein the matching rate is calculated based on a similarity between the partial fingerprint measurement data and the reference comparison data or based on a matching area between the partial fingerprint measurement data and the reference comparison data.

6. The fingerprint authentication method of claim 1, further comprising:
  defining an entire fingerprint area that is formed by arranging all of the plurality of partial fingerprint registration data to overlap common regions therebetween;
  acquiring, if the matching rate is smaller than the predetermined authentication threshold, a comparison fingerprint area by arranging all of the partial fingerprint registration data that have been selected as the reference comparison data to overlap common regions therebetween; and
  determining and outputting a failure of the authentication when a ratio of the comparison fingerprint area to the entire fingerprint area is equal to or greater than a predetermined value.

7. The fingerprint authentication method of claim 6, wherein one of the plurality of partial fingerprint registration data is selected as the reference comparison data depending on a distance from a center of the entire fingerprint area.

8. A computer program stored on a non-transitory computer-readable storage medium which, when executed by a processor, performs the fingerprint authentication method of claim 1.

9. A non-transitory computer-readable storage medium storing instructions which, when executed by a processor, perform the fingerprint authentication method of claim 1.

10. A fingerprint authentication device comprising:
a data storage unit configured to store a plurality of partial fingerprint registration data, each of which corresponds to a part of a fingerprint;
a data input unit configured to receive partial fingerprint measurement data for an authentication, which corresponds to a part of a fingerprint;
a control unit configured to perform the authentication by comparing the plurality of partial fingerprint registration data and the partial fingerprint measurement data; and
an output unit configured to output a result of the authentication under a control of the control unit,
wherein the control unit performs steps of:
calculating a matching rate by comparing the partial fingerprint measurement data with reference comparison data selected among the plurality of partial fingerprint registration data;
first determining whether the matching rate is equal to or greater than a predetermined authentication threshold; and
second determining, based on a result in the step of first determining, a success of the authentication to complete the authentication, or repeating the calculating step and the first determining step by selecting new reference comparison data among the partial fingerprint registration data that have not been selected as the reference comparison data based on whether or not the matching rate is equal to or greater than a preset threshold, which is smaller than the predetermined authentication threshold.

11. The fingerprint authentication device of claim 10, wherein the control unit is configured to select the reference comparison data based on a sum or an average of matching rates which are calculated by matching each of the partial fingerprint registration data with all of the other partial fingerprint registration data or based on the number of matched data when matching each of the partial fingerprint registration data with all of the other partial fingerprint registration data.

12. The fingerprint authentication device of claim 10, wherein, in the repeating step, if the matching rate is equal to or greater than the preset threshold, one of the plurality of partial fingerprint registration data whose matching rate with the reference comparison data previously used is equal to or greater than a first threshold is selected as the new reference comparison data, and
if the matching rate is smaller than the preset threshold, one of the plurality of partial fingerprint registration data whose matching rate with the reference comparison data previously used is smaller than a second threshold is selected as the new reference comparison data.

13. The fingerprint authentication device of claim 12, wherein the second threshold is equal to or smaller than the first threshold.

14. The fingerprint authentication device of claim 10, wherein the matching rate is calculated based on a similarity between the partial fingerprint measurement data and the reference comparison data or based on a matching area between the partial fingerprint measurement data and the reference comparison data.

15. The fingerprint authentication device of claim 10, wherein the control unit further performs steps of:
defining an entire fingerprint area that is formed by arranging all of the plurality of partial fingerprint registration data to overlap common regions therebetween;
acquiring, if the matching rate is smaller than the predetermined authentication threshold, a comparison fingerprint area by arranging all of the partial fingerprint registration data that have been selected as the reference comparison data to overlap common regions therebetween; and
determining and outputting a failure of the authentication a ratio of the comparison fingerprint area to the entire fingerprint area is equal to or greater than a predetermined value.

16. The fingerprint authentication device of claim 15, wherein one of plurality of the partial fingerprint registration data is selected as the reference comparison data depending on a distance from a center of the entire fingerprint area.

* * * * *